(12) United States Patent
Kim et al.

(10) Patent No.: US 8,771,996 B2
(45) Date of Patent: Jul. 8, 2014

(54) MARINE BACTERIUM OF METABOLIZING 3,6-ANHYDRO-L-GALACTOSE AND USE OF THE SAME

(75) Inventors: Kyoung Heon Kim, Seoul (KR); In Geol Choi, Seoul (KR); Eun Ju Yun, Seoul (KR); Sae Young Lee, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 13/557,803

(22) Filed: Jul. 25, 2012

(65) Prior Publication Data

US 2013/0102036 A1 Apr. 25, 2013

(30) Foreign Application Priority Data

Jul. 26, 2011 (KR) ........................ 10-2011-0074288

(51) Int. Cl.
*C12P 19/02* (2006.01)
(52) U.S. Cl.
USPC .......................................................... 435/105
(58) Field of Classification Search
None
See application file for complete search history.

(56) References Cited

FOREIGN PATENT DOCUMENTS

| KR | 1020080093525 A | 10/2008 |
|---|---|---|
| KR | 1020100108241 A | 10/2010 |

OTHER PUBLICATIONS

Roh et al., "Genome Sequence of *Vibrio* sp. Strain EJY3, an Agarolytic Marine Bacterium Metabolizing 3,6-Anhydro-L-Galactose as a Sole Carbon Source", J. Bacteriology, May 2012, vol. 194(1), pp. 2773-2774.*

Xiao Ting Fu, et al; "Agarase: Review of Major Sources, Categories, Purification Method, Enzyme Characteristics and Applications", Marine Drugs, vol. 8, pp. 200-218; Published Jan. 26, 2010; ISSN 1660-3397; www.mdpi.com/journal/marinedrugs.

Lora M. Morrice, et al; "β-Agarases I and II from *Pseudomonas atlantica* Substrate specificities", Eur. J. Biochem, vol. 137, pp. 149-154, Oct. 1983.

Nathan A. Ekborg, et al; Genomic and Proteomic Analyses of the Agarolytic System Expressed by *Saccharophagus degradans* 2-40; Applied and Enviromental Microbiology, vol. 72, Issue 5, pp. 3396-3405; May 2006; DOI:10.1128/AEM.72.5.3396-3405.2006.

Jingxue Wang, et al; "Characterization of a novel β-agarase from marine *Alteromonas* sp. SY37-12 and its degrading products", Appl. Microbiol. Biotechnol. vol. 71, pp. 833-839; Published online Nov. 24, 2005.

Hee Taek Kim, et al; "Overexpression and molecular characterization of Aga50D from *Saccharophagus degradans* 2-40: an exo-type β-agarase producing neoagarobiose", Appl. Microbiol Biotechnol, vol. 86, pp. 227-234, Published online: Oct. 3, 2009.

Saeyoung Lee, et al; "Crystallization and preliminary X-ray analysis of neoagarobiose hydrolase from *Saccharophagus degradans* 2-40", Acta Crystallographica Section F Structural Biology and Crystallization Communications, vol. F65, pp. 1299-1301; Dec. 2009.

* cited by examiner

*Primary Examiner* — Suzanne M Noakes
(74) *Attorney, Agent, or Firm* — Ladas & Parry LLP (57) ABSTRACT

Disclosed is a novel marine microorganism which can metabolize 3,6-anhydro-L-galactose and use of the same. The novel marine microorganism belongs to *Vibrio* sp. which utilizes 3,6-anhydro-L-galactose (3,6-L-AHG) as a single carbon source to convert 3,6-L-AHG to ribose and 3,6-anhydrogalactonic acid.

6 Claims, 11 Drawing Sheets

FIG 1

| Colony Nos. | 1 | 3 | 6 | 7 | 11 |
|---|---|---|---|---|---|
| Sampling site | seaweed | crab | mud flat | mud flat | sea water |
| Colony color | ivory | ivory | ivory | ivory(turns red with time) | orange |
| Clear zone test | excellent agar-degrading activity; formation of clear zone | formation of clear zone on solid medium | formation of clear zone on solid medium | no clear zone formed | no clear zone formed |

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Primer
```

```
<400> SEQUENCE: 1
agagtttgat catggctcag                                              20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
agagtttgat cctggctcag                                              20

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
acggctacct tgttacgact t                                            21

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
acggttacct tgttacgact t                                            21
```

MARINE BACTERIUM OF METABOLIZING 3,6-ANHYDRO-L-GALACTOSE AND USE OF THE SAME

CROSS-REFERENCE TO RELATED APPLICATION

This application claims priority to and the benefit of Korean Patent Application No. 10-2011-0074288, filed Jul. 26, 2011, the disclosure of which is incorporated herein by reference in its entirety.

BACKGROUND

1. Field of the Invention

The present invention relates to a novel marine bacterium of metabolizing 3,6-anhydro-L-galactose (3,6-L-AHG) and use of the same.

2. Discussion of Related Art

The world is currently facing a global energy security crisis due to increased energy consumption in developing countries as well as the depletion of petroleum resources. Therefore, there is an urgent need for the development of a biofuel which can replace petroleum resources. In this regard, many nations including the U.S., Europe, Brazil, Japan and China have endeavored their efforts to develop biofuels in order to secure various energy resources and cope with global climate change, and a higher level of investment and research and development are expected to continue in the future. With the advent of post-Kyoto Protocol, South Korea is soon expected to become a country to be forced to reduce its carbon dioxide emissions and thus there is an urgent call for the nation for the development of biofuels. Bioethanol is one of biofuels available to replace petroleum resources, its market has been expanding worldwide and is expected to grow about 17.2% annually. For example, the U.S. plans to replace about 20% of its nationwide gasoline consumption with bioethanol by 2020, and many oil companies including BP and Shell and various venture companies have already joined the research on production of the next generation biofuel. Bioethanol has been mainly thought to be produced using food resources and so issue of the scarcity of food resources and increase in food prices has been raised thus necessitating research into the production of biofuels using inedible resources. Inedible biomass resources are largely classified into ligneous biomass and seaweed biomass. For South Korea with a relatively small territory surrounded by water on its three sides, seaweed biomass is more suitable considering its geographical features. Also, South Korea belongs to the top ranking global seaweed producing countries along with China, Japan and North Korea with its annual gross product amounting to 13,754 tons as of 2006. However, there still remains a large amount of room in terms of its utilization (Fisheries Production Statistics, 2006, Agriculture and Fisheries Production Statistics Division Population and Social Statistics Bureau, National Statistical Office, Korea).

The biomass of red algae includes, based on its dry weight, 60% of agar and 20% of cellulose, i.e., being comprised 80% of it as carbohydrates. Agar, the highest content of red algae, consists of agarose and agaropectin. Both polysaccharides have a structure linked by β-1,4 and α-1,3 bonds in which D-galactose and 3,6-anhydro-L-galactose (hereinafter referred to as '3,6-L-AHG') alternate therein (T. Fu and S. M. Kim, Marine Drugs 2010, 8, 200-218). Therefore, galactose which is fermentable in microorganisms and monosaccharides of 3,6-L-AHG which is not well known in the art can be obtained by hydrolyzing these polymers.

There are two known methods to degrade agarose polymers so far: a chemical method to hydrolyze using a strong acid, such as sulfuric acid and hydrochloric acid, and heat; and an enzymatic method to degrade it using agarase, an enzyme which digests agarose. Agaose is degraded using enzymes derived from microorganisms with agar-degrading capability such as Pseudoalteromonas atlantica (L. M. Morrice et al. *Eur J. Biochem.* 137. 149-154, 1983), *Saccharophagus degradans* (N. A. Ekborg. *Appl Environ Microbiol.* 72(5) 3396-3405, 2006), and *Alteromonas* sp. (J. Wang et al. *Appl Microbiol Biotechnol.* 71. 833-839, 2006). Agarose-degrading enzymes can be largely divided into three groups: an enzyme that produces oligosaccharides via hydrolysis of the internal bonds of agarose polymers, an enzyme that degrades a polymer or oligosaccharide into a disaccharide (HT. Kim et al. *Appl Microbiol Biotechnol.* 86. 227-234, 2010), and an enzyme that degrades a disaccharide into a monosaccharide such as D-galactose and 3,6-L-AHG (Lee, S et al. *Acta Crystallogr* Sect F-Struct Biolo Cryst Commun. 65. 1299-1301, 2009).

Korean Patent Application Publication No. 10-2010-0108241 (titled as "NOVEL ALPHA-NEO AGAROBIOS HYDROLASE AND A METHOD FOR OBTAINING MONOSACCHARIDE USING THE SAME") discloses a novel α-neoagarobiose hydrolase and a method of obtaining 3,6-L-AHG using the same. These enzymes are derived from *S. degradans*, *Pseudoalteromonas atlantica* T6c. Korean Patent Application Publication No. 10-2008-0093525 (titled as "STREPTOMYCES SP. STRAIN (ACCESSION NO. KCTC 11091BP) HAVING THE ALGINATE HYDROLYSIS ACTIVITY, AN ALGINATE LYASE DERIVED FROM THE SAME, AND A TRANSFORMANT PREPARED BY USING A POLYNUCLEOTIDE ENCODING THE ALGINATE LYASE") discloses *Streptomyces* sp. with alginate hydrolysis activity, which degrades alginate into saturate alginate oligomer and unsaturate alginate oligomer, alginate lyase produced by *Streptomyces* sp., and a recombinant enzyme expressed in *E. coli* by cloning the gene encoding the alginate lyase.

Meanwhile, the greatest disadvantage that results from the production of bioenergy using seaweed biomass is that it has a low yield in ethanol fermentation using seaweed biomass because 3,6-L-AHG that is one of monosaccharides contained in agarose is a non-fermentable sugar. The metabolism for fermenting D-galactose has already been elucidated. However, so far there has been no report on any bacterial strain which can metabolize using 3,6-L-AHG as a single carbon source and thus there has been no remarkable progress on the studies of identifying the metabolic pathway of the material. Therefore, it is essential to identify the metabolic pathway of L-AHG and, based on the same, develop a method for improving the production yield of bioethanol by converting the non-fermentable sugar into a fermentable sugar.

SUMMARY OF THE INVENTION

The present invention is directed to providing a novel marine microorganism which can metabolize 3,6-L-AHG, and a method of culturing the same.

The present invention is also directed to providing a method for producing ribose and 3,6-anhydrogalactonic acid, as metabolites of 3,6-L-AHG, by using the above novel 3,6-L-AHG-metabolizing microorganism.

To achieve the above, the present invention provides a novel marine microorganism *Vibrio* sp. EJY3, which has a 3,6-L-AHG metabolic activity, and has been deposited under the Accession No. of KCTC 11976BP.

The present invention further provides a method of culturing a novel marine microorganism *Vibrio* sp. EJY3. Here, the method includes culturing the marine microorganism *Vibrio* sp. EJY3 using 3,6-L-AHG as a carbon source.

The present invention still further provides a method of producing ribose and 3,6-anhydrogalactonic acid. Here, the method includes producing ribose and 3,6-anhydrogalactonic acid by reacting a culture broth of *Vibrio* sp. EJY3, a novel marine microorganism, or a crude enzyme extract thereof with 3,6-L-AHG.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, the present invention will be described with reference to examples and comparative examples in detail. However, the present invention is not limited to these examples.

The present invention provides a novel marine microorganism *Vibrio* sp. EJY3, which has a 3,6-L-AHG metabolic activity, and has been deposited under the Accession No. of KCTC 11976BP.

The present invention also provides a method of culturing a novel marine microorganism *Vibrio* sp. EJY3. Here, the method includes culturing the same using 3,6-L-AHG as a carbon source.

The novel marine microorganism of the present invention was isolated by sampling seaweeds, mud flat, rotten crabs, sea water, etc., at Dongmak beach located in Dongmak-ri, Hwado-myeon, Ganghwa-gun, Incheon, Korea, culturing the samples in a minimal broth for 12 hours, diluting the culture broths in minimal solid media to be plated, primarily screening the resulting bacteria to select agar-degrading bacteria, selecting the strains that use 3,6-L-AHG as a single carbon source, and identifying the finally selected strains through the 16S rRNA sequencing thereof.

From the 16S rRNA sequencing results, the microorganism of the present invention was confirmed to be a novel marine microorganism that belongs to *Vibrio* sp. and was named *Vibrio* sp. EJY3 accordingly. The microorganism of the present invention, named *Vibrio* sp. EJY3, was deposited under Accession No. KCTC 11976BP to the Korean Collection for Type Culture (KCTC) of the Korea Research institute of Bioscience and Biotechnology (KRIBB) located at 52, Eoeun-dong, Yuseong-gu, Daejeon, Korea, on Jun. 30, 2011.

Agar, a representative polysaccharide taking up to 60% of the total weight of red algae biomass, can be degraded into two monosaccharides: D-galactose and 3,6-L-AHG. When these monosaccharides are converted into a fuel such as ethanol or a biochemical product, 3,6-L-AHG, unlike in galactose, is not fermented or metabolized by general microorganisms such as *E. coli* and yeast used in the industry. Therefore, in a process of obtaining ethanol from red algae via fermentation or biological conversion, it is essential to convert 3,6-L-AHG into a fermentable or metabolizable sugar by a microorganism so as to achieve a two-fold increase in production yield.

In order to confirm whether the novel marine microorganism of the present invention metabolizes 3,6-L-AHG, the cells of the novel marine microorganism of the present invention were sonicated to homogenate the cell walls, centrifuged to obtain a water soluble protein. Then, an enzymatic reaction was performed on the water soluble protein using 3,6-L-AHG, as a substrate, and NADH cofactor.

As a result, it was confirmed that the novel marine microorganism of the present invention, *Vibrio* sp. EJY3, metabolized 3,6-L-AHG into ribose and 3,6-anhydro galactonic acid.

Therefore, the present invention provides a method of producing ribose and 3,6-anhydrogalactonic acid. Here, the method includes producing ribose and 3,6-anhydro galactonic acid by reacting a culture broth of *Vibrio* sp. EJY3, a novel marine microorganism of the present invention, or a crude enzyme extract thereof with 3,6-L-AHG.

The culture broth of *Vibrio* sp. EJY3, a novel marine microorganism of the present invention, may be obtained from a conventional microorganism culture which uses 3,6-L-AHG as a single carbon source, but the present invention is not limited thereto.

Further, the crude enzyme extract of *Vibrio* sp. EJY3, a novel marine microorganism of the present invention, may include a water soluble protein obtained by sonicating the culture broth to homogenate the cell walls and centrifuging the homogenate, but the present invention is not limited thereto.

The metabolization of 3,6-L-AHG by using a culture broth of *Vibrio* sp. EJY3, a novel marine microorganism of the present invention, or a crude enzyme extract thereof may further require NADH as a cofactor.

As mentioned above, by directly employing the metabolic pathway and enzymes of the marine microorganism or by artificially inserting a gene of an enzyme involved in the metabolism into a different fermentation microorganism to construct a recombinant strain, the present invention can be used to improve production yield by converting 3,6-L-AHG into ribose and 3,6-anhydro galactonic acid.

Further, ribose, a metabolite of 3,6-L-AHG, is a sugar that is metabolizable and fermentable in all kinds of microorganisms, and can be metabolized by the microorganisms in production of a biofuel using seaweed biomass, thereby improving production yield of biofuels.

Hereinafter, the present invention will be described in further detail with respect to examples according to the present invention and comparative examples not according to the present invention, but the scope of the present invention is not limited by the following examples.

EXAMPLES

Example 1

Screening of Agar-Metabolizing Microorganism

In order to screen agar-metabolizing microorganisms, sampling was conducted at Dongmak beach, Western seashore of Korea, and nearby mud flats. Seaweeds, crabs, mudflat and sea water were collected and stored in a 50 ml tube, respectively. To culture the microorganisms in the samples, a minimal medium, in which 2.3% (w/v) of sea water salt, 0.05% (w/v) of ammonium chloride, 0.1% (w/v) of yeast extract, and 0.2% (w/v) of agar were dissolved in 50 mM Tris-HCl buffer (pH 7.4), was used. To each of 50 ml sample tubes carrying the respective samples was added 20 ml of a 2.3% (w/v) NaCl solution, sufficiently vortexed, the supernatant was recovered, and then seeded in a liquid medium. The samples were cultured in a liquid medium for 12 hours, and then plated on a solid medium. The solid medium was prepared by adding 1.5% (w/v) agar to a composition of the liquid medium.

Each bacterium forming colonies was streaked on a fresh solid medium using a sterile platinum loop, and cultured for 48 hours. A 2% (v/v) iodine solution was poured on the solid medium, and the formation of a clear zone around the colonies was observed thereby confirming the agar-degrading activity of the microorganism.

Figure 1:
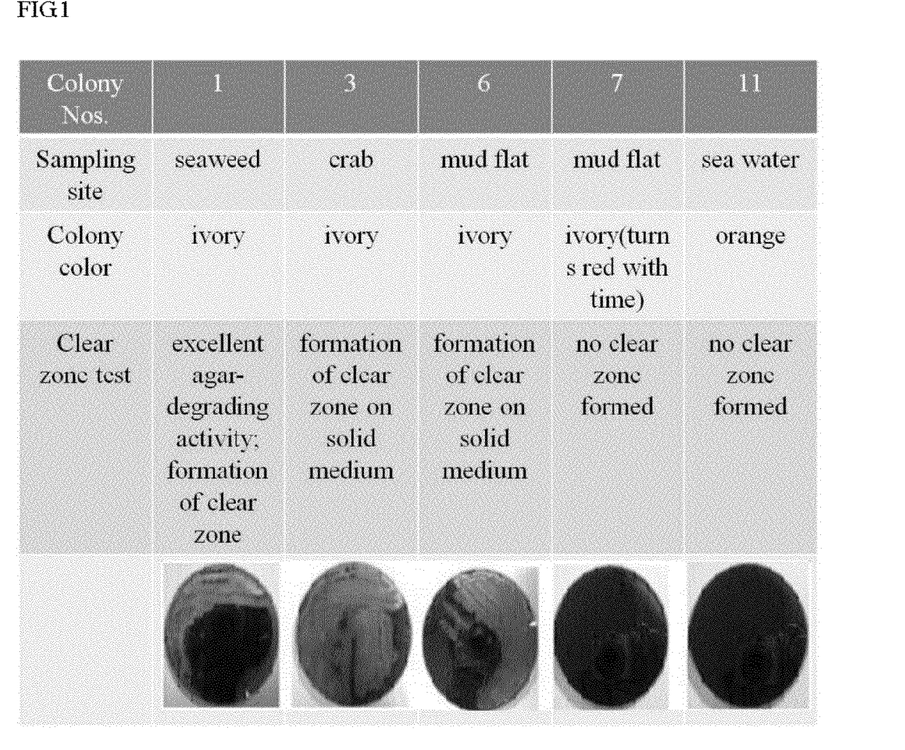
FIG. 1 shows a result of screening agar-metabolizing microorganisms.

As a result, 3 out of the 5 strains utilizing agar as a single carbon source (colony Nos. 1, 3 and 6) were observed to form clear circles (FIG. 1)

Example 2

Test of *Vibrio* sp. EJY3 Utilizing 3,6-L-AHG as Single Carbon Source

Agar-metabolizing microorganisms screened via the test of agar degrading activity in Example 1 were seeded in a single carbon source of 3,6-L-AHG. The medium used was a minimal medium, in which 2.3% (w/v) of sea water salt, 0.05% (w/v) of ammonium chloride, 0.1% (w/v) of yeast extract, and 0.2% (w/v) of 3,6-L-AHG were dissolved in 50 mM Tris-HCl buffer (pH 7.4).

As a result, it was observed that the bacterium in colony No. 3 grew in the medium. The amount of 3,6-L-AHG remaining in the medium according to culture time was examined via TLC to confirm whether the stain metabolizes 3,6-L-AHG.

TLC developing solvent used was prepared by mixing n-butanol, ethanol, and water in the ratio of 3:1:1 (v/v/v). One hour after development, a chromogenic reaction was performed at 95° C. for 30 seconds using two kinds of chromogenic solvents in which 10% (v/v) sulfuric acid and 2% (w/v) naphthoresorcinol were dissolved in ethanol.

Figure 2:
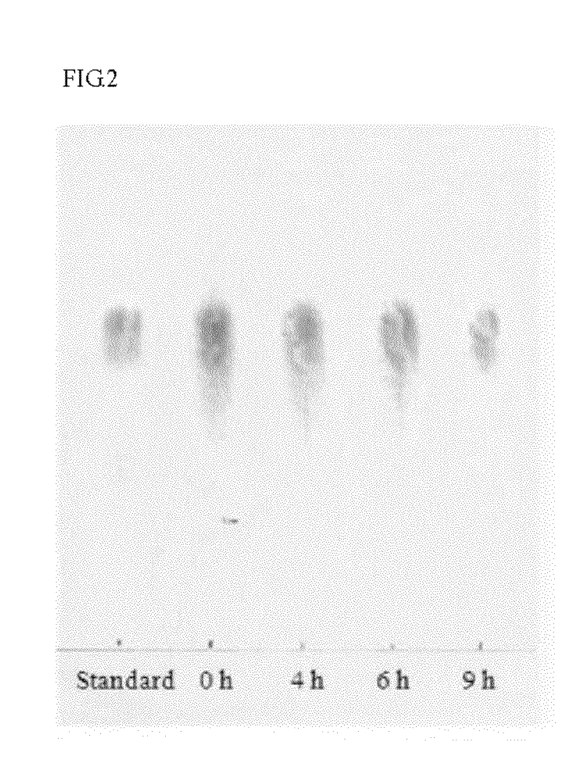
FIG. 2 shows a result of using 3,6-L-AHG as a single carbon source by *Vibrio* sp. EJY3, wherein standard indicates 3,6-anhydro-D-galactose.

Referring to FIG. 2, Lane No. 1 of the TLC result indicates a standard material of 3,6-anhydrogalactose present in D-form, which was purchased from Dextra Laboratories of the U.K. The time indicated in Lane Nos. 2 to 5 refers to culture time. Each liquid culture sample was collected according to the culture time, and centrifuged to recover the supernatant. TLC analysis was performed to examine the amount of 3,6-L-AHG remaining in the supernatant.

As shown in FIG. 2, it was confirmed that the amount of 3,6-L-AHG remaining in the medium decreased with an increase in culture time, which indicates that the screened stain grows by metabolizing 3,6-L-AHG.

Example 3

16S rRNA Sequencing of *Vibrio* sp. EJY3

In Examples 1 and 2, it was confirmed that colony No. 3 metabolized 3,6-L-AHG. To identify the bacterial strain, 16S rRNA sequencing of the bacterium strain was analyzed. Genomic DNA was extracted from the bacterial cells and the 16S rDNA domain was amplified using two PCR primers of 27 forward primer {5'-AGAGTTTGATCATGGCTCAG-3' (SEQ. ID NO: 1) or 5'-AGAGTTTGATCCTGGCTCAG-3' (SEQ. ID NO: 2] and 1492 reverse primer {5'-ACGGCTAC-CTTGTTACGACTT-3'(SEQ. ID NO: 3) or (5'-ACGGTTAC-CTTGTTACGACTT-3' (SEQ. ID NO: 4)}, and then sequenced.

Figure 3:
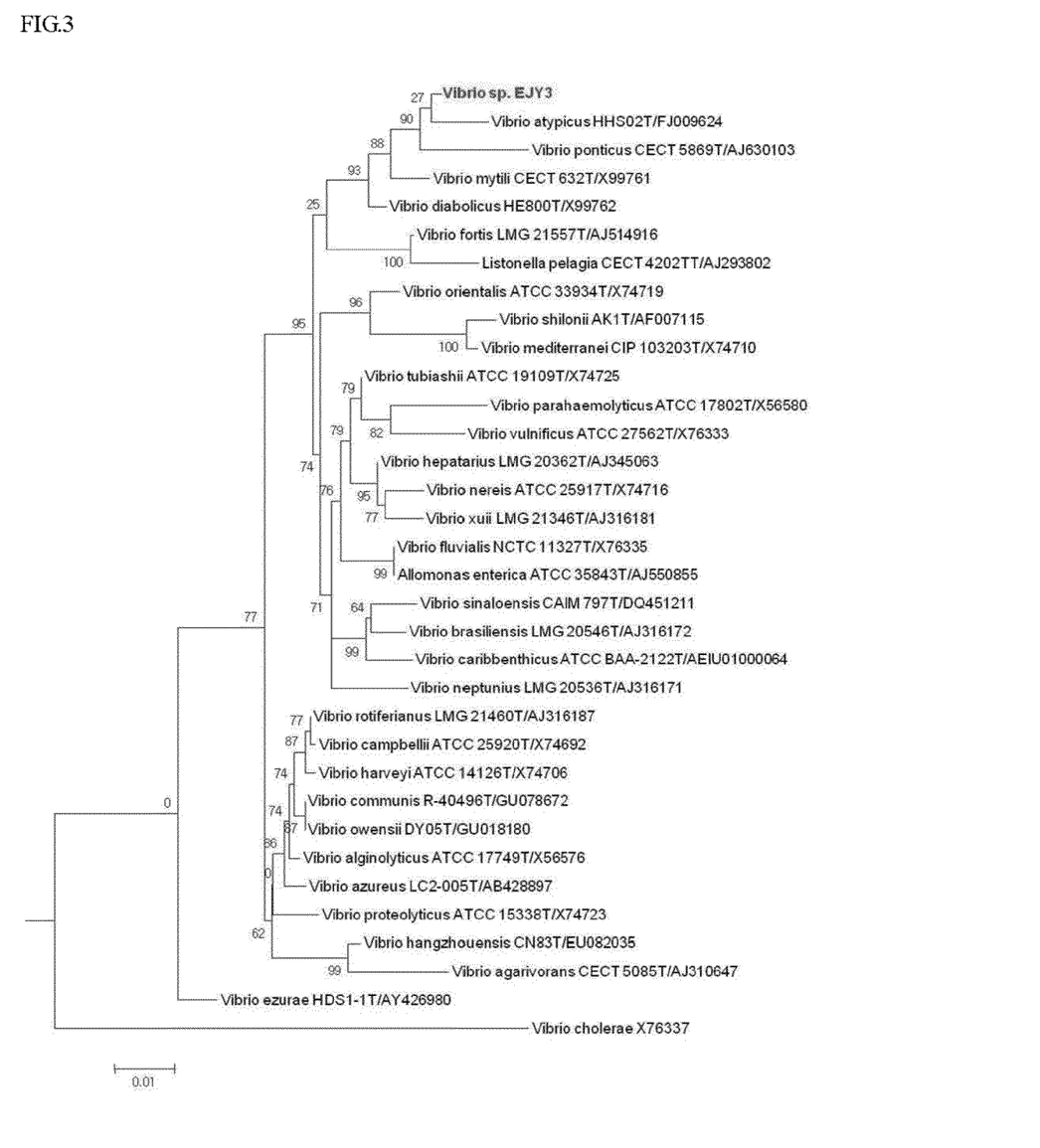
FIG. 3 shows a phylogenetic analysis result of *Vibrio* sp. EJY3 based on the 16S rRNA sequencing of *Vibrio* sp. EJY3.

As a result of the phylogenetic analysis based on the 1401 bp long nucleotide sequences of the 16S rRNA, the bacterial strain was found to be a novel strain very close to *Vibrio atypicus* (FIG. 3), and was named as *Vibrio* sp. EJY3 accordingly.

Example 4

Confirmation Via TLC After Reacting Crude Enzyme Extract of *Vibrio* sp. EJY3 with 3,6-L-AHG In order to obtain a crude enzyme, *Vibrio* sp. EJY was cultured in a minimal medium, in which 2.3% (w/v) of sea water salt, 0.05% (w/v) of ammonium chloride, 0.1% (w/v) of yeast extract, and 0.2% (w/v) of 3,6-L-AHG were dissolved in 50 mM Tris-HCl buffer (pH 7.4), for 12 hours, and centrifuged to separate cells from the medium. After centrifugation (5,000 rpm, 30 min, 4° C.) of 200 ml of the cell culture broth, the supernatant was discarded and the cells were suspended in 20 ml of 20 mM Tris-HCl, and sonicated (amplitude: 40% for 2 minutes) to homogenate the cell walls. Then, the homogenate was re-centrifuged (16,000 rpm, 30 min, 4° C.) and the supernatant containing the crude enzyme was collected and subjected to enzymatic reaction.

3,6-L-AHG, which was used as a substrate in the enzymatic reaction, is a monosaccharide contained in agarose, and can be obtained as a final product along with D-galactose by hydrolysis of agarose. The hydrolysis of agarose is as follows: Agarose polymer is pretreated with 3N acetic acid to obtain agarooligosaccharide, which is then treated with Aga 50D (The European Molecular Biology Laboratory (EMBL) nucleotide sequence database identification No.: CP000282, synthesized from 2382 nucleotides), an exo-type agarase to obtain disaccharides. Then, the disaccharides were treated with neoagarobiose hydrolase (NABH) to obtain monosaccharides of D-galactose and 3,6-L-AHG. Of the reaction products obtained by pretreatment using weak acid and enzymatic treatment, 3,6-L-AHG was purified via silica gel chromatography. Here, a solvent including chloroform, ethanol, and water in the ratio of 78:20:2 (v/v/v) was used as the mobile phase. Of them, a fraction containing 3,6-L-AHG was concentrated and then purified again with Bio-Gel-P2 size exclusion chromatography thereby obtaining 3,6-L-AHG to be used as a substrate for enzymatic reaction. The reaction was conducted using 50 μl (40 μg) of a crude enzyme extract, 15 mM 3,6-L-AHG, 3 mM NADH, 20 mM Tris-HCl buffer (pH 7.4) at 30° C., 200 rpm, for 12 hours.

Figure 4:
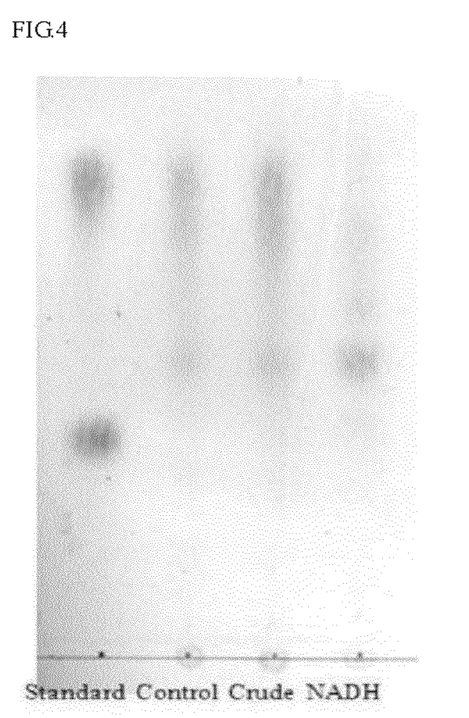
FIG. 4 shows a result of TLC after reacting a crude enzyme extract of *Vibrio* sp. EJY3 with 3,6-L-AHG.

Referring to FIG. 4, Lane No. 1 of the TLC result indicates standard materials of D-galactose and D-form 3,6-anhydrogalactose, Control of Lane No. 2 represents a group in which no reaction occurs because the enzyme is deactivated, Crude of Lane No. 3 represents a reaction product obtained by reacting substrate with a crude enzyme solution without adding an NADH cofactor, and NADH of Lane No. 4 represents a reaction product obtained by reacting a crude enzyme, a substrate and an NADH cofactor.

As shown in FIG. 4, it was revealed that the crude enzymatic reaction of *Vibrio* sp. EJY3 occurs in the presence of the NADH cofactor but does not occur in the absence of the NADH cofactor.

Example 5

GC/MS Analysis of Reaction Product Obtained by Reacting Crude Enzyme Extract of *Vibrio* sp. EJY3 with 3,6-L-AHG As described in Example 4, 50 μl (40 μg) of the crude enzyme extract of *Vibrio* sp. EJY3, 15 mM 3,6-L-AHG, 3 mM NADH, and 20 mM Tris-HCl buffer (pH 7.4) were reacted at 30° C., 200 rpm for 12 hours. The reaction product was identified by GC/MS analysis. In order to prepare a sample for GC/MS analysis, 200 μl out of the total 500 μl of the total reaction product was dried using a speed bag, 20 mg/ml (w/v) O-Methylhydroxylamine hydrochloride in pyridine was added and reacted at 75° C. for 30 minutes. Then, 80 μl of N-methyl-N-(trimethylsilyl)trifluoroacetamide was added thereto and further reacted at 40° C., 150 rpm for 30 minutes. The GC/MS analysis conditions were as follows: The column used for analysis was DB-5MS capillary column, and a GC oven was operated under the condition of maintaining 100° C. for 3.5 minutes; increasing it to a temperature of 160° C. and maintaining the temperature for 20 minutes; increasing it again to a temperature of 200° C. and maintaining the temperature for 15 minutes; and further increasing it to a temperature of 280° C. and maintaining the temperature for 5 minutes. The injector temperature was 250° C., a split ratio was 1:9.6, and the injection amount was 1 μl. The scan range of a mass detector was 50 to 600 m/z.

Figure 5:
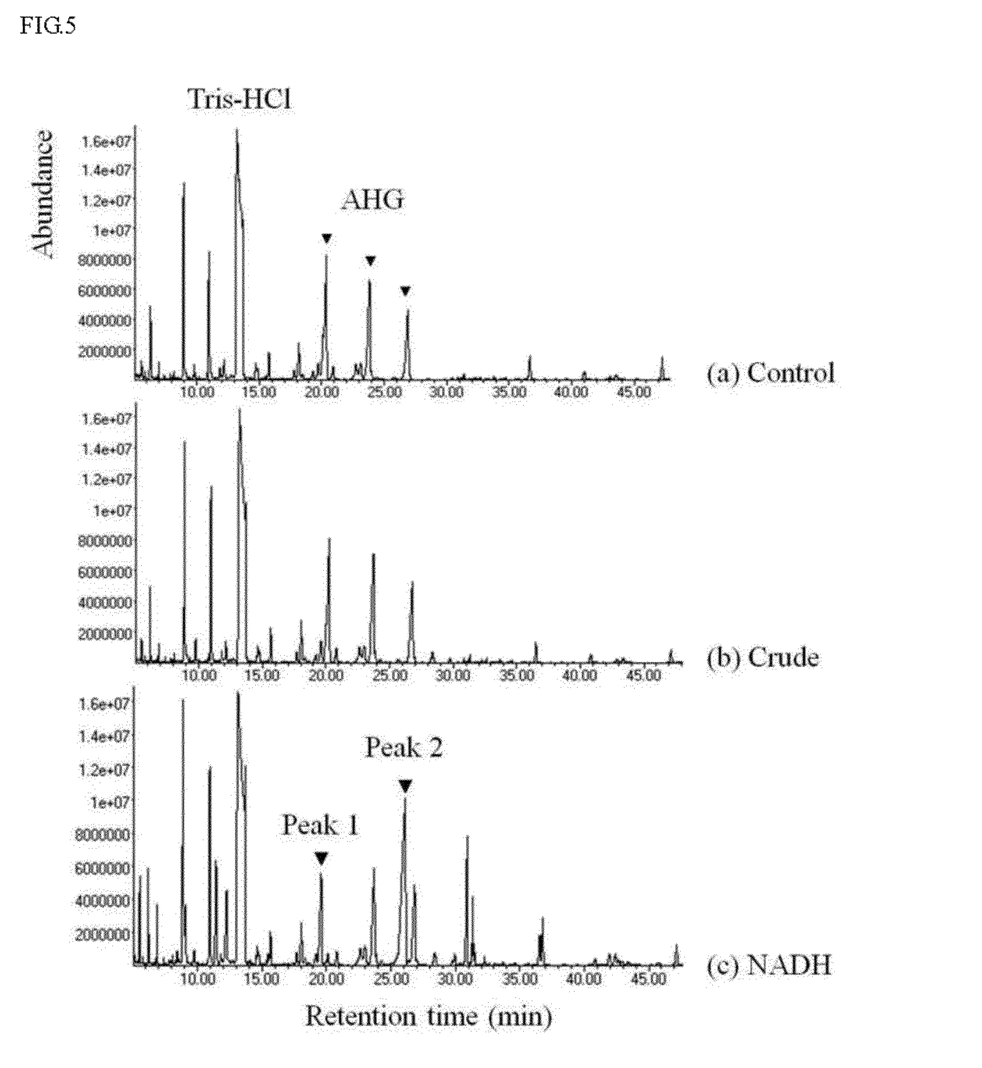
FIG. 5 shows a result of GC/MS analysis of a reaction product obtained by reacting a crude enzyme extract of *Vibrio* sp. EJY3 with 3,6-L-AHG.

FIG. 5 shows a total ion chromatogram obtained based on GC/MS analysis: (a) Control indicates a group in which there was no reaction because the enzyme was inactivated, in which Tris-HCl means a Tris-HCl buffer (pH 7.4), and AHG refers to 3,6-L-AHG; (b) Crude indicates a reaction product obtained by reaction of a crude enzyme and a substrate without adding NADH cofactor; and (c) NADH indicates a reaction product obtained by reaction of a crude enzyme and a substrate in the presence of the NADH cofactor.

As shown in FIG. 5, no enzymatic reaction occurred in (b) Crude but, when the reaction was conducted in the presence of the NADH cofactor, a peak level of 3,6-L-AHG dropped and other new peaks were formed. The new peaks formed in (c) NADH were named as peak 1 and peak 2.

Example 6

Confirmation of Metabolite to be Ribose by Comparison Between the Mass Spectra of Metabolite and D-Ribose 50 μl (40 μg) of the crude enzyme extract derived from *Vibrio* sp. EJY3 in Example 5, 15 mM 3,6-L-AHG, 3 mM NADH, and 20 mM Tris-HCl buffer (pH 7.4) were reacted at 30° C., 200 rpm for 12 hours to obtain a reaction product. From the GC/MS total ion chromatogram ((c) NADH) of the reaction product, it was confirmed that a region of the peak 1 was ribose by analyzing the standard substance under the same conditions (Aldrich, R1757).

Figure 6:
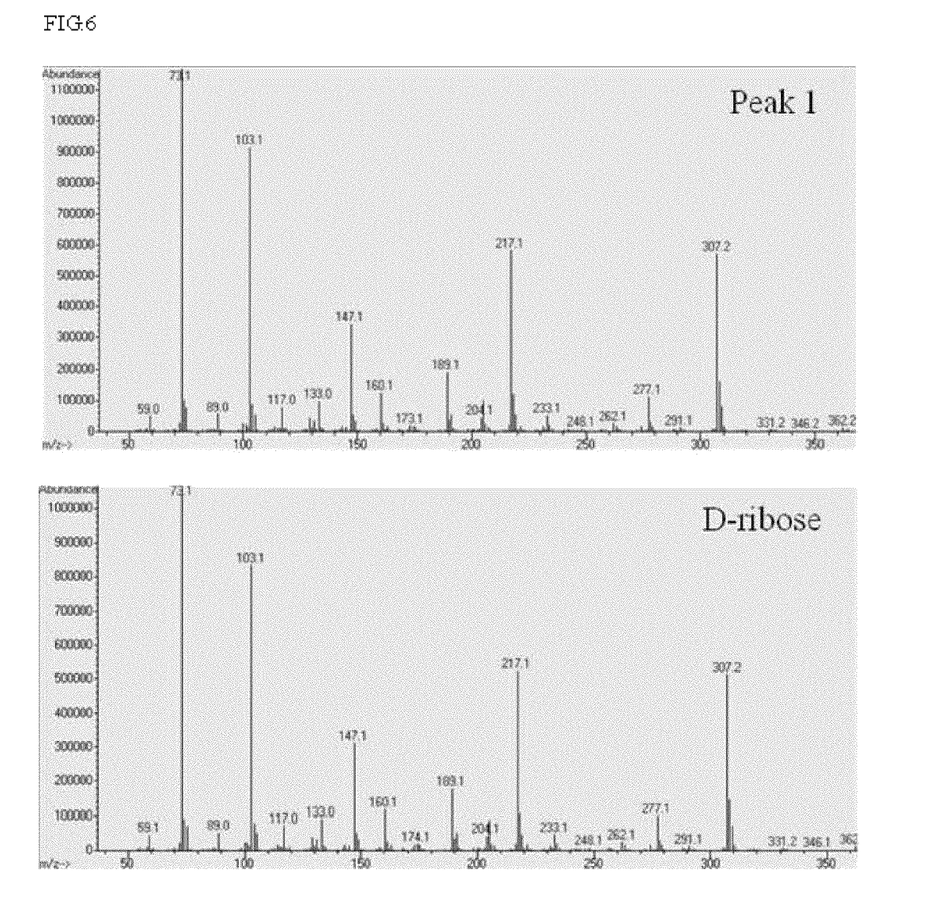
FIG. 6 shows spectrum results that confirms that the metabolite (Peak 1) is ribose by comparing the mass spectrum of the metabolite with that of D-ribose.

FIG. 6 shows the mass spectra of the peak 1 and ribose. From the fact that the mass spectrum of the peak 1 corresponded to that of the ribose, it was confirmed that the peak 1 that was a reaction product newly formed by the enzymatic reaction was ribose.

Example 7

Confirmation of Metabolite to be 3,6-Anhydro Galactonic Acid by Comparison Between Mass Spectra of Metabolite and Purified 3,6-anhydro-L-galactonic Acid (AHGA)

50 μl (40 μg) of the crude enzyme extract derived from *Vibrio* sp. EJY3 in Example 5, 15 mM 3,6-L-AHG, 3 mM NADH, and 20 mM Tris-HCl buffer (pH 7.4) were reacted at 30° C., 200 rpm for 12 hours to obtain a reaction product. From the GC/MS total ion chromatogram ((c) NADH) of the reaction product, it was confirmed that a region of the peak 2 was 3,6-anhydro galactonic acid by analyzing the purified 3,6-anhydro galactonic acid under the same conditions.

Figure 7:
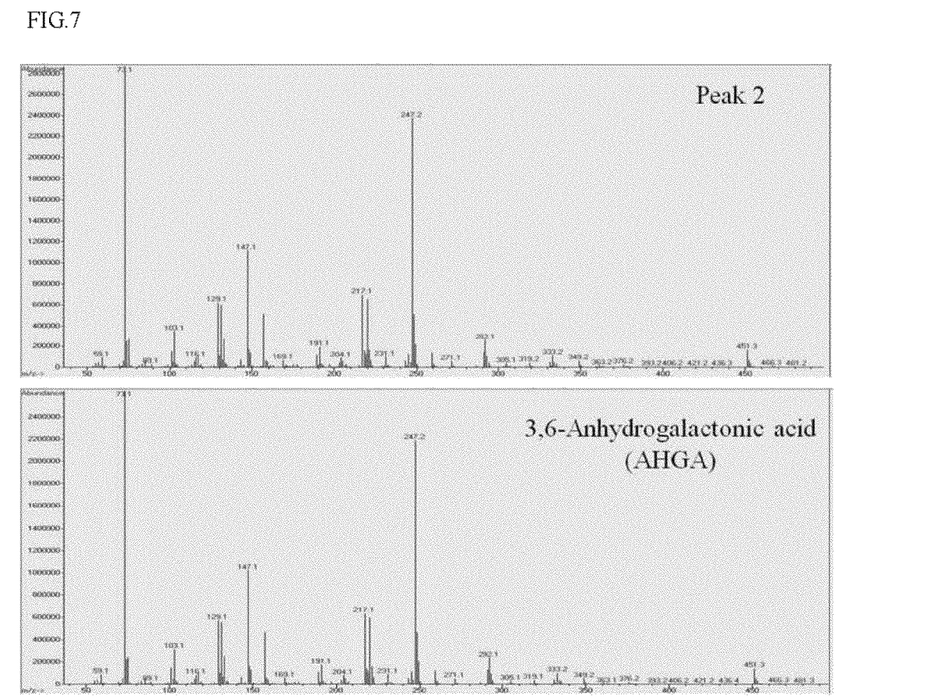
FIG. 7 shows spectrum results that confirms that the metabolite (Peak 2) is 3,6-anhydrogalactonic acid by comparing the mass spectrum of the metabolite with that of 3,6-anhydrogalactonic acid.

FIG. 7 shows the mass spectra of peak 2 and 3,6-anhydro galactonic acid. From the fact that the mass spectrum of the peak 2 corresponded to that of 3,6-anhydro galactonic acid, it was confirmed that the peak 2 that was a reaction product newly formed by the enzymatic reaction was 3,6-anhydro galactonic acid known as a reaction product of 3,6-anhydro L-galactose dehydrogenase.

Example 8

Confirmation of Via TLC After Reacting Crude Enzyme Extract of *Vibrio* sp. EJY3 with Agarose Hydrolysate To obtain an agarose hydrolysate, a crude enzyme extract of *Saccharophagus degradans* 2-40, known as a marine microorganism with excellent agar-degrading activity, was reacted with 0.5% (w/v) agarose to prepare D-galactose and 3,6-L-AHG, which are monosaccharides contained in agarose. 50 ml of a crude enzyme extract of *Saccharophagus degradans* 2-40 with a concentration of 1.7 mg/ml was added to 50 ml of a substrate, in which 0.5% agarose is dissolved in 20 mM Tris-HCl buffer, and allowed to react at 30° C., 200 rpm for 12 hours. The resulting monosaccharides (D-galactose and 3,6-L-AHG) were simultaneously analyzed quantitatively via GC/MS. The method of preparing a crude enzyme extract and the GC/MS analysis were the same as described in Examples 4 and 5.

As a result of the agarose hydrolysis, 1.7 mg/ml D-galactose and 1.9 mg/ml 3,6-L-AHG were produced. The hydrolysates were reacted with a crude enzyme extract of *Vibrio* sp. EJY3 and the resulting reaction product was analyzed via TLC. The reaction conditions were as follows: 10 ml of the agarose hydrolysate, 1 ml (2 mg) of the crude enzyme extract of *Vibrio* sp. EJY3, and 1 mM NADH cofactor were dissolved in 20 mM Tris-HCl buffer (pH 7.4), and then allowed to react for 12 hours. The crude enzyme extract of *Vibrio* sp. EJY3 was prepared in the same manner as described in Example 4.

Figure 8:
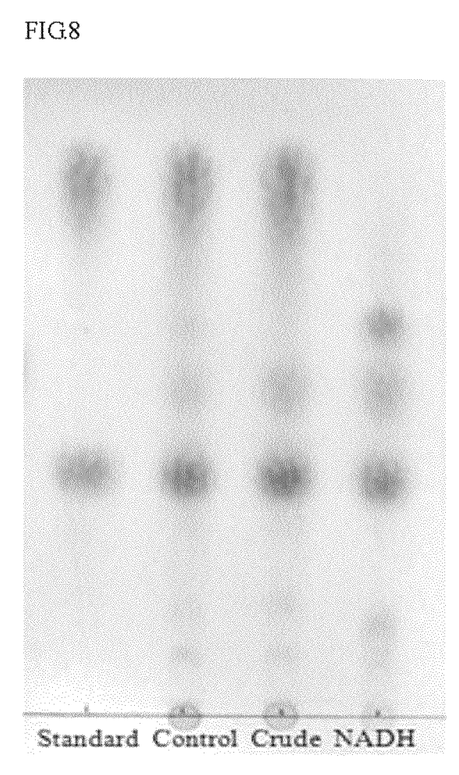
FIG. 8 shows a result of TLC after reacting a crude enzyme extract of *Vibrio* sp. EJY3 with an agarose hydrolysate.

Referring to FIG. 8, 'Standard' indicates standard substances of D-galactose and 3,6-L-AHG, 'Control' indicates a group in which no reaction took place because the enzyme was inactivated, 'Crude' indicates a reaction product obtained by reaction of a crude enzyme and a substrate without adding an NADH cofactor; and 'NADH' indicates a reaction product obtained by reaction of a crude enzyme and a substrate in the presence of the NADH cofactor.

From the TLC result of FIG. 8, it was confirmed that there was no change in the agarose hydrolysate, which was used as a substrate, when the NADH cofactor was not added, whereas, when the NADH cofactor was added, 3,6-L-AHG, among the agarose hydrolysates, was converted to a different material.

Example 9

GC/MS Analysis of a Reaction Product Obtained by Reaction Between Crude Enzyme Extract of *Vibrio* sp. EJY3 and Agarose Hydrolysate As described in Example 8, 1 ml (2 mg) of the crude enzyme extract of *Vibrio* sp. EJY3 was reacted with 10 ml of agarose hydrolysate and 1 mM NADH in 20 mM Tris-HCl buffer at 30° C., 200 rpm for 12 hours. Then, the reaction product was identified via GC/MS analysis. The methods of converting a sample into derivatives and performing GC/MS analysis were the same as described in Example 5.

Figure 9:
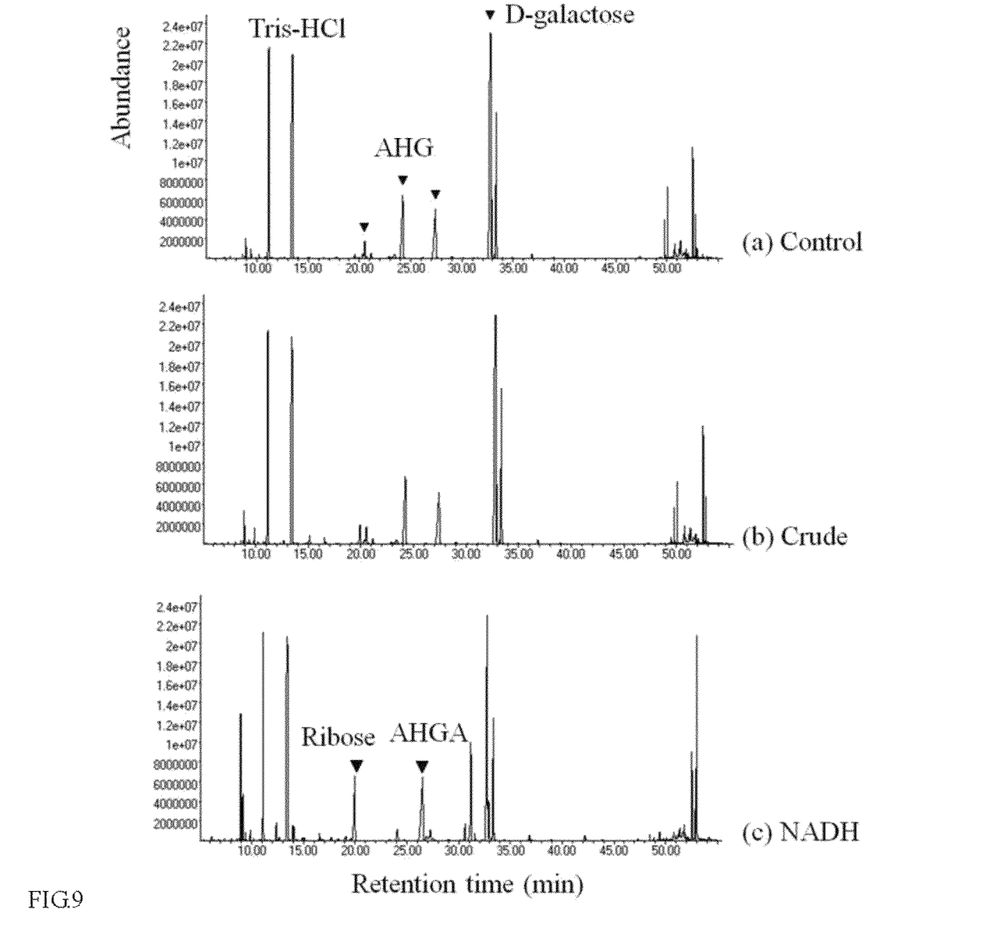
FIG. 9 shows a result of GC/MS analysis of a reaction product obtained by reacting a crude enzyme extract of *Vibrio* sp. EJY3 with an agarose hydrolysate.

Referring to FIG. 9, (a) Control indicates a group in which no reaction took place because the enzyme was inactivated, where Tris-HCl means a Tris-HCl buffer (pH 7.4), and AHG refers to 3,6-L-AHG; (b) Crude indicates a reaction product obtained by reaction of a crude enzyme and a substrate without adding an NADH cofactor; and (c) NADH indicates a product obtained by reaction of a crude enzyme and a substrate in the presence of the NADH cofactor.

As shown in FIG. 9, it was confirmed that no enzymatic reaction occurred in (a) Crude but, when the reaction was conducted in the presence of the NADH cofactor, a peak level of 3,6-L-AHG dropped and other new peaks were formed. Also, it was confirmed that the new peaks formed in (c) NADH were those of the ribose and 3,6-anhydro galactonic acid.

Example 10

Figure 10:
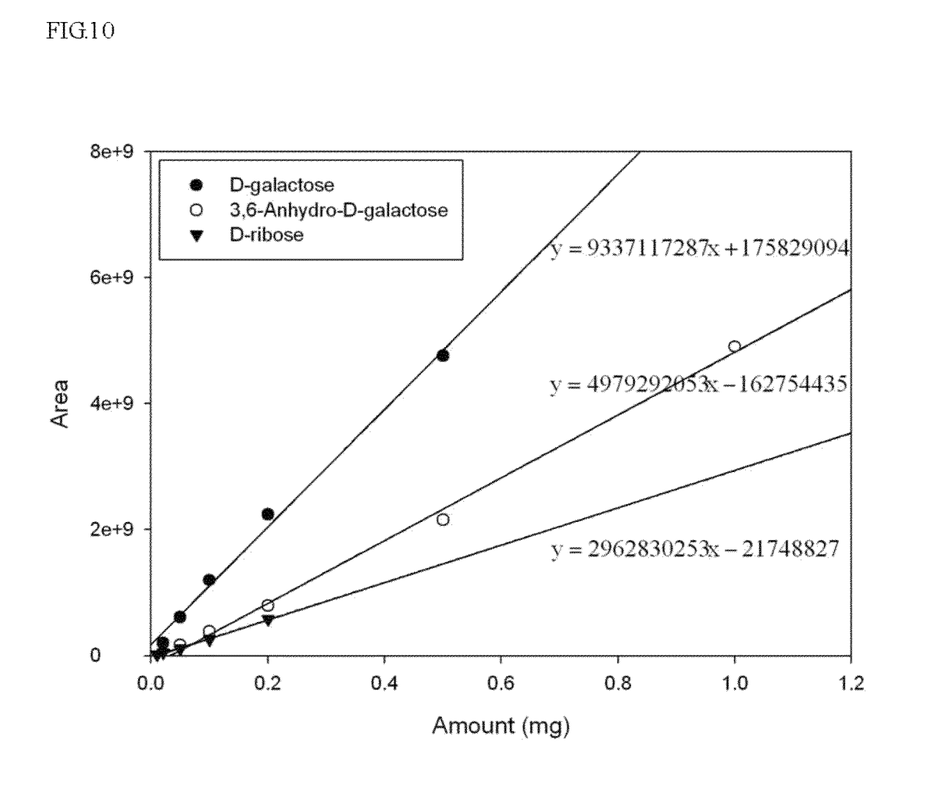
FIG. 10 shows a quantitative curve on GC/MS obtained using standard substances of D-galactose, 3,6-anhydro-D-galactoes, D-ribose.

Quantitation Via GC/MS Using Standard Substances of D-Galactose, 3,6-anhydro-D-galactose and D-ribose To quantify D-galactose, 3,6-anhydro-D-galactose and D-ribose, the standard substances were analyzed per concentration, and the quantitative curves of the standard substances were plotted from the area values of the peaks thereof. D-galactose, 3,6-anhydro-D-galactose and D-ribose were purchased from Acrose Organics, Dexta Laboratories and Aldrich, respectively. Each standard substance was prepared as a stock solution with a concentration of 10 mg/ml. The standard substances were dissolved in 20 mM Tris-HCl buffer (pH 7.4) under the same conditions as in the enzymatic reaction for *Vibrio* sp. EJY3, and then diluted with the same buffer solution to prepare an increasing concentration of the standard substances for GC/MS quantitative analysis. The amount of each of the standard substances was 1 mg, 0.5 mg, 0.2 mg, 0.1 mg, 0.05 mg, and 0.025 mg. After the GC/MS quantitative analysis, the quantitative curves of the standard substances were plotted from the peak area values of GC/MS total ion chromatogram by setting up a straight line region (FIG. 10). The GC/MS analysis was the same as in Example 5.

The reaction products of Example 8 were quantified based on the quantitative lines of D-galactose, 3,6-anhydro-D-galactose and D-ribose obtained above.

Figure 11:
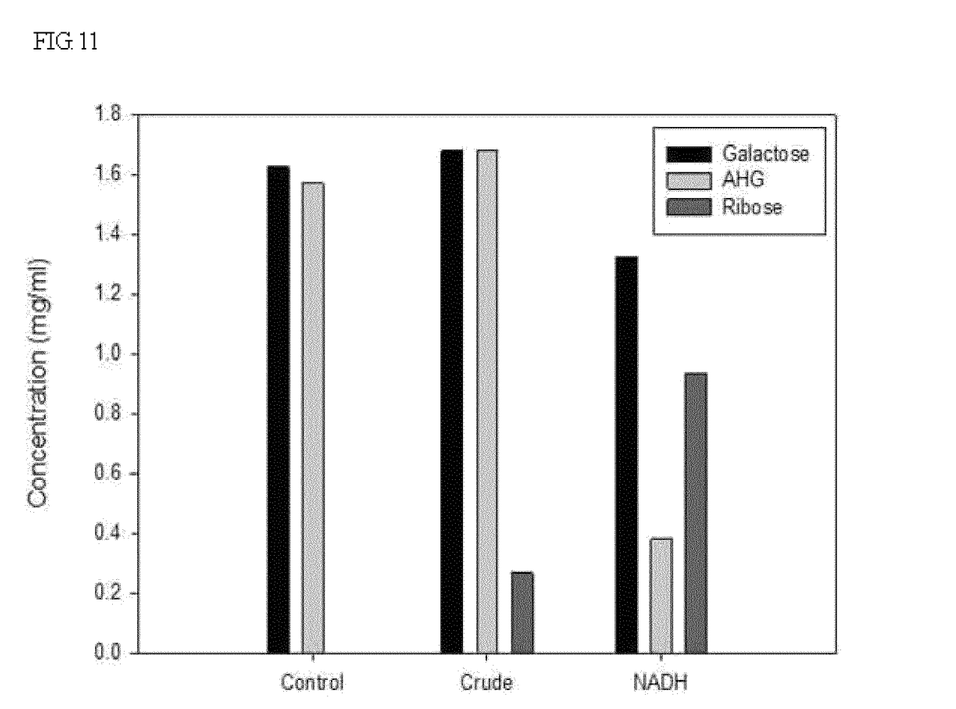
FIG. 11 shows a result of quantitative analysis of a reaction product obtained by reacting the crude enzyme extract of *Vibrio* sp. EJY3 with an agarose hydrolysate based on the GC/MS results obtained in FIG. 10.

Referring to FIG. 11, 'Control' indicates a group in which no reaction took place because the enzyme was inactivated, 'Crude' indicates a reaction product obtained by reaction of a crude enzyme and a substrate without adding an NADH cofactor; and 'NADH' indicates a reaction product obtained by reaction of a crude enzyme and a substrate in the presence of the NADH cofactor.

As shown in FIG. 11, the quantification results revealed that no ribose was produced in 'Control' while ribose was produced in both 'Crude' and 'NADH' conditions, with the greatest production observed in 'NADH' condition. From the quantification results of the reaction products based on their quantitative curves, it was quantitatively revealed that no ribose was produced but 1.62 mg/ml of galactose and 1.57 mg/ml of 3,6-L-AHG substrates were present in 'Control'. On the other hand, 0.26 mg/ml of ribose was produced in 'Crude', and 0.93 mg/ml of ribose was produced when the reaction took place after addition of 'NADH'.

While the invention has been shown and described with reference to certain exemplary embodiments thereof, it will be understood by those skilled in the art that various changes in form and details may be made therein without departing from the scope of the invention as defined by the appended claims.

What is claimed is:

1. A marine microorganism, *Vibrio* sp. EJY3, that has been grown using 3,6-anhydro-L-galactose (3,6-L-AHG) as a single carbon source and is deposited under the Accession No. KCTC 11976BP.

2. The marine microorganism, *Vibrio* sp. EJY3, according to claim 1, wherein the marine microorganism metabolizes 3,6-L-AHG to produce ribose and 3,6-anhydro galactonic acid.

3. A method of culturing a novel marine microorganism, *Vibrio* sp. EIY3, according to claim 1, the method comprising:
culturing the marine microorganism, *Vibrio* sp. EIY3, using 3,6-L-AHG as a carbon source.

4. A method of producing ribose and 3,6-anhydrogalactonic acid, comprising: producing ribose and 3,6-anhydrogalactonic acid by reacting a culture broth of the novel marine microorganism, *Vibrio* sp. EIY3, according to claim 1 or a crude enzyme extract thereof with 3,6-L-AHG.

5. The method according to claim 4, wherein the crude enzyme extract includes a water soluble protein obtained by sonicating and centrifuging the culture broth of the novel marine microorganism.

6. The method acid according to claim 4, wherein the reaction is conducted by further adding NADH.

* * * * *